United States Patent [19]

Nicolaou et al.

[11] Patent Number: 4,567,290

[45] Date of Patent: Jan. 28, 1986

[54] LEUKOTRIENE ANALOGUES

[75] Inventors: Kyriacos C. Nicolaou, Haverton; Nicos A. Petasis; Steven P. Seitz, both of Philadelphia, all of Pa.

[73] Assignee: Research Corporation, New York, N.Y.

[21] Appl. No.: 528,733

[22] Filed: Sep. 1, 1983

Related U.S. Application Data

[62] Division of Ser. No. 325,553, Nov. 27, 1981, Pat. No. 4,442,099.

[51] Int. Cl.$^4$ .......................................... C07C 69/743
[52] U.S. Cl. .................................................. 560/124
[58] Field of Search ....................... 560/124; 562/506

[56] References Cited

U.S. PATENT DOCUMENTS

| | | | |
|---|---|---|---|
| 3,671,558 | 6/1972 | Siddall | 560/124 |
| 3,737,450 | 6/1973 | Henrick | 560/124 |
| 4,001,428 | 1/1977 | Kosower | 560/124 |

OTHER PUBLICATIONS

Nicolaou, J. Chem. Soc., Chem. Commun., (22), pp. 1195–1196 (1981).

*Primary Examiner*—Michael L. Shippen
*Attorney, Agent, or Firm*—Scully, Scott, Murphy & Presser

[57] ABSTRACT

A compound of the formula

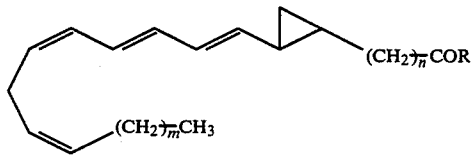

wherein
n is an integer from 2 to 4;
m is an integer from 3 to 5;
R is OM, OR$_1$ or NR$_2$R$_3$ where M is a pharmaceutically acceptable cation;
R$_1$, R$_2$ and R$_3$ are the same or different and selected from the group consisting of hydrogen, C$_1$–C$_2$ branched, unbranched or cyclic alkyl aryl and aralkyl; or R$_2$ and R$_3$ taken together from a group of the formula

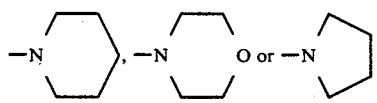

can be used as an inhibitor of the lipoxygenase pathway of the arachidonic acid cascade in animals.

1 Claim, No Drawings

LEUKOTRIENE ANALOGUES

This is a division of application Ser. No. 325,553, filed on Nov. 27, 1981, now U.S. Pat. No. 4,442,099.

BACKGROUND OF THE INVENTION

1. Field of the Invention

The present invention relates to leukotriene analogues, which are stable, biologically active and useful as antiasthmatic or antiallergic agents.

2. Description of the Prior Art

Recent investigations in the lipoxgenase pathway of the arachidonic acid cascade led to the discovery of leukotrienes, a new class of biologically active eicosanoids (c.f. B. Samuelsson, Pure Appl. Chem., 53: 1203 (1981); P. Borgeat et al, J. Med. chem., 24: 121 (19981); and E. J. Corey et al, J. Amer. Chem. Soc., 102: 1436 (1980)).

The first leukotriene formed in this biosynthetic sequence is leukotriene A4 (LTA4, formula 1):

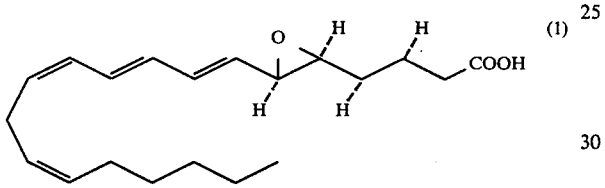

LTA4 is a relatively unstable substance with an epoxide unit. This substance serves as a precursor to leukotrienes B4 (LTB4) which are potent chemotactic agents, and to a number of "slow reacting substances of anaphylaxis" (SRS-A) which have been implicated in asthma and other hypersensitivity reactions.

Chemical synthesis has already been achieved for most of the natural leukotrienes, and a number of their isomers (c.f. E. J. Corey et al, J. Amer. Chem. Soc., 102: 1436 (1980); J. Rokach et al, Tetrahedron Lett. 22: 979 (1981); and M. Rosenberger et al, J. Amer. Chem. Soc., 102: 5425 (1980)).

A need, however, continues to exist for stable biologically active leukotriene analogues, in view of their potentially highly useful pharmacological properties.

SUMMARY OF THE INVENTION

It is an object of the invention to provide stable biologically active leukotriene analogues.

It is another object of the invention to provide pharmaceutical compositions containing stable, biologically active leukotriene analogues.

It is yet another object of the invention to provide a process for the synthesis of stable biologically active leukotriene analogues.

It is still another object of the invention to provide a method of treating hypersensitivity reactions by using stable, biologically active leukotriene analogues. Those and other objects of the invention which will hereinafter become more readily apparent, have been attained by providing:

A compound of the formula (2):

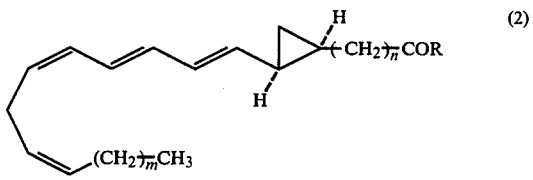

wherein n is an integer from 2 to 4;
m is an integer from 3 to 5;
R is OM, OR$_1$ or NR$_2$R$_3$;
where M is a pharmaceutically acceptable cation; R$_1$, R$_2$ and R$_3$ are the same or different and selected from the group consisting of hydrogen, C$_1$-C$_{12}$ branched, unbranched or cyclic alkyl, aryl and aralkyl; or R$_2$ and R$_3$ taken together form a group of the formulae:

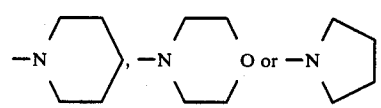

DESCRIPTION OF THE PREFERRED EMBODIMENTS

The present invention provides leukotriene analogues which, instead of an epoxide ring, carry a cyclopropane ring. This feature of the analogues render them highly stable in biological media, and greatly facilitates their transport, storage and administration.

The compounds of the invention have the following formula (2):

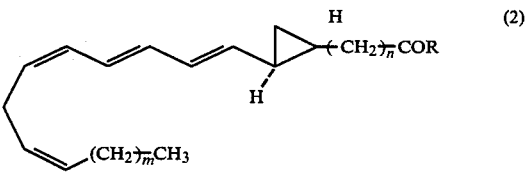

wherein n is an integer from 2 to 4, most preferably 3.
m is an integer from 3 to 5, most preferably 4.
R is OM, OR$_1$ or NR$_2$R$_3$,
where M is a pharmaceutically acceptable cation.

Pharmaceutically acceptable cations useful for the purposes of this invention are for example pharmaceutically acceptable metal cations or amine cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1, 3-propanediol, 2-amino-2-methyl-1-propanol, tris(hydroxymethyl) aminomethane, N-phenylethanolamine, N-(p-tert-amylphenyl)diethanolamine, galactamine, N-methyl-glucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The $C_1$-amide derivatives of prostaglandin $PGF_2\alpha$ have been shown to be antagonistic to the action of the natural $PGF_2$ α free acids by Ramwell, P. and his co-workers (Ramwell, P. et al, Nature, 278, 549 (19780)). The use of the C-1 amides in the present invention is thus one of the preferred embodiments.

$R_1$, $R_2$ and $R_3$ are the same or different and selected from the group consisting of hydrogen, $C_1$—$C_{12}$ branched, unbranched or cyclic alkyl, aryl and aralkyl. Preferred alkyl groups are lower alkyl groups, most preferred branched or unbranched $C_1$—$C_4$ alkyl groups, such as methyl, ethyl, propyl, isopropyl, n-butyl, and the like. Preferred cyclic alkyl groups are cyclohexyl, cyclopentyl, and the like. Preferred aryl groups are phenyl, lower-alkyl substituted phenyl (e.g. tolyl, and the like); halo-substituted phenyl (e.g. chlorophenyl, bromophenyl, and the like); and combinations thereof. Preferred aralkyl groups include benzyl, lower alkyl substituted benzyl, halo-substituted benzyl, and the like. $R_2$ and $R_3$, taken together may also form a cycloalkyl radical such as

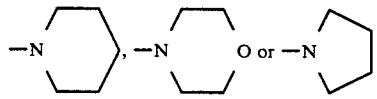

It is to be noted that, in the molecules of the invention, the configuration around the cyclopropane ring is trans, and that the molecules contain two trans-double bonds, and two cis-double bonds.

Specific compounds of the invention are

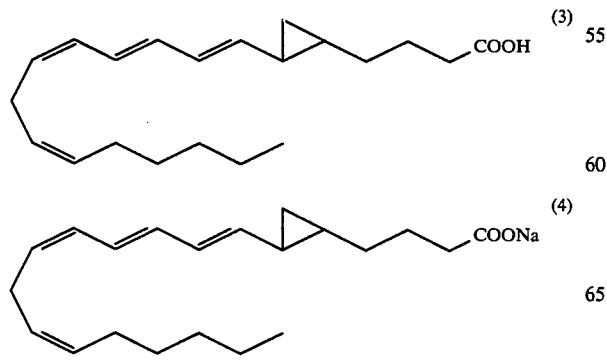

The compounds of the invention can be prepared for example by the following Scheme 1:

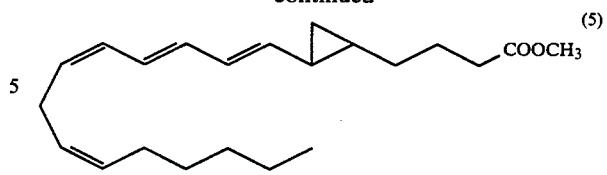

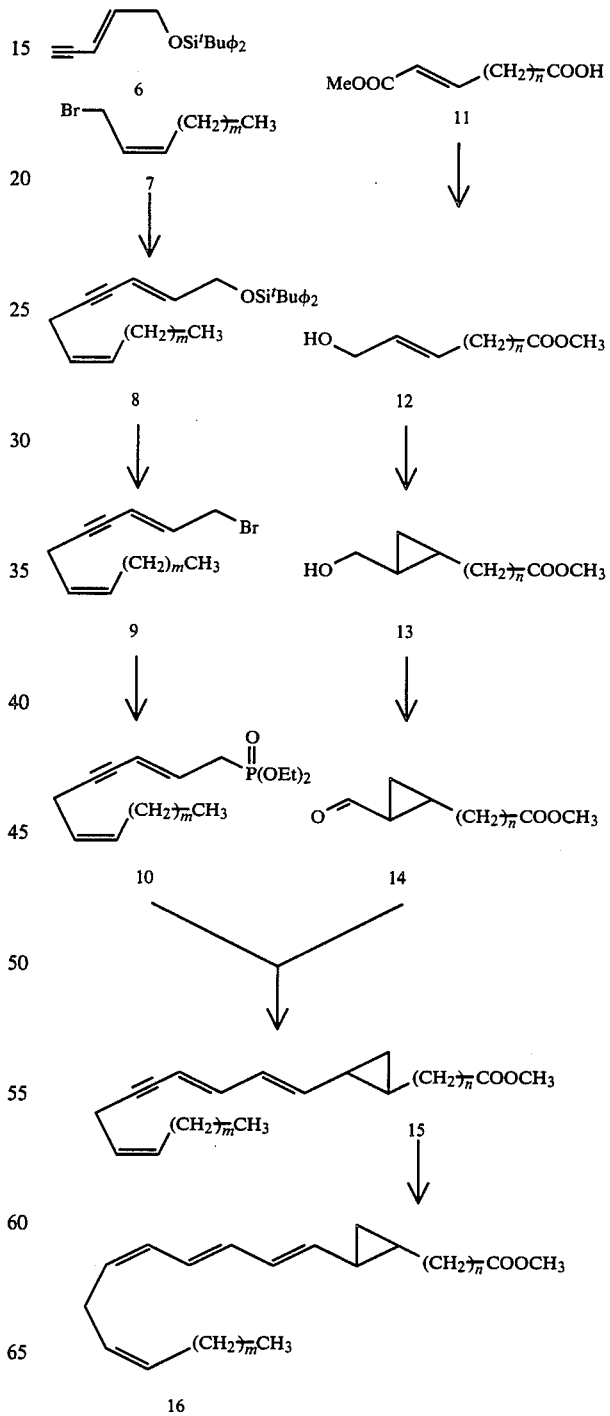

2-Penten-4-yn-l-ol can be converted to an appropriately protected alcohol by using for example t-butyldiphenylsilyl chloride (ClSi$^t$Bu$\phi_2$), and the product, e.g. $^t$Butyldiphenylsilyl ether 6, is coupled with 2(E)-1-bromo-2-heptene, 2(E)-1-bromo-2-octene or 2(E)-1-bromo-2nonene, (depending on the desired value of m in the final product). The coupling is carried out in an inert solvent, such as DMF, HMPA, DMSO or the like, at 0° C.–30° C., with a slight excess of the silyl ether in the presence of a base. The 2(E)-1-bromo-2-alkene 7 is prepared from the corresponding n-alkyllithium with LiClCuI-HMPA/THF at about −80° C.

Coupling of 6 and 7 yields the ether 8. Removal of the O-protecting group and replacement of the resulting hydroxide by a bromine yields the bromide 9, which is then transformed to phosphonate 10 by treatment, for example, with trimethylphosphite.

The other component required to assemble the leukotriene analogue, aldehyde 14, can be constructed from an appropriate ester/acid 11. Treatment of the monoester 11 with a reducing agent (such as DIBAL, excess, −80° C.) followed by esterification, gives the allylic alcohol 12, which can then be smoothly cyclopropanated with CH$_2$I/Zn/CuCl, to afford the alcohol cyclopropane derivative 13. This alcohol 13 can then be oxidized to aldehyde 14 by normal methods (e.g. Jones oxidation, and the like).

Condensation of aldehyde 14 with phosphonate 10 can occur under standard Wittig conditions and results in a stereocontrolled coupling, forming compound 15, which can be further purified, as by column chromatography. Selective hydrogenation of the acetylenic linkage of 15 leads to ester 16. Hydrolysis of 16 yields the corresponding acid and/or salts.

The esters and amides of the invention can readily be prepared by methods well known to those skilled in the art, for example preparation of the acid chloride followed by treatment with amines or alcohols.

The compounds of the invention can be used in the treatment of any disease or condition alleviated by a selective inhibition of the lipoxygenase pathway of the arachidonic acid cascade, without inhibition of the corresponding cyclooxygenase pathway. For example, the compounds of the invention can be used as antiasmathics, antiallergics, and generally as anti-chemotactics and anti-anaphilactics.

The compounds of this invention can be administered by any means that effects inhibition of the lipoxygenase pathway in warm-blooded animals. For example, administration can be parenterally, subcutaneously, intravenously, intramuscularly, intraperitoneally or, most preferably by aerosol. Alternatively or concurrently, administration can be by the oral route. The dosage administered will be dependent upon the age, health and weight of the recipient, kind of concurrent treatment if any, frequency of treatment, and the nature of the effect desired. Generally, daily dosage of active ingredient compounds will be from about 0.5 mg to 50 mg per kg of body weight. Normally, from 1 to 30 mg per kg per day, in one or more applications per day will be effective to obtain the desired result. The compounds can be employed in dosage forms such as tablets, capsules, powder packets, or liquid solutions, aerosol suspensions, or elixirs, for oral administration, or sterile liquid for formulations such as solutions or suspensions for parenteral use. In such compositions, the active ingredient will ordinarily always be present in an amount of at least 0.5% by weight based on the total weight of the composition and not more than 90% by weight.

Having generally described the invention, a more complete understanding can be obtained by reference to certain examples, which are included for purposes of illustration only and are not intended to be limiting unless otherwise specified.

SYNTHESIS OF 5,6 METHANOLEUKOTRIENE A$_4$, ACID AND METHYL ESTER

The synthesis was carried out according to Scheme 2:

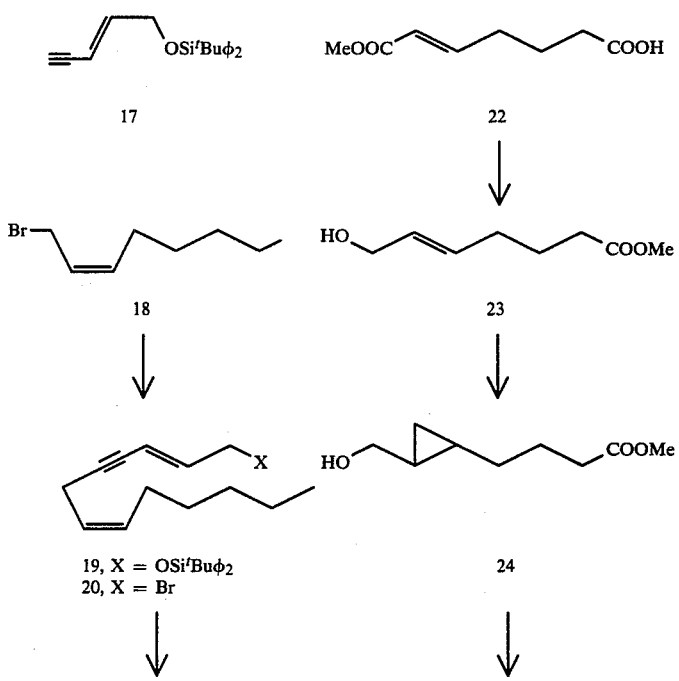

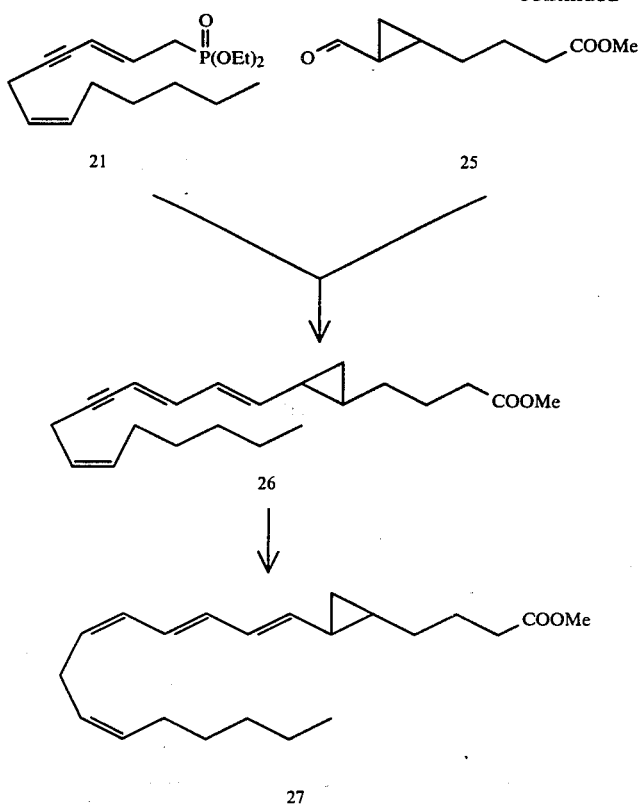

2-Penten-4-yn-1-ol was converted to its tert-butyldiphenylsilyl ether 17 (1.1 equiv. $^tBU\phi_2SiCl$, imidazole, DMF, 25° C., 100%) and coupled to 2(E)-1-bromo-2-octene (18) (nBuli—LiCl—CuI—HMPA, THF, −78° C., 60%) to afford product 19. Removal of the silyl ether (HF-pyridine, THF, 25° C., 90%) followed by treatment with $CBr_4$-$P\phi_3$ (1.2 equiv. of each, $CH_2Cl_2$, 0° C., 98%) led to the bromide 20 which was converted to the desired phosphonate 21 by exposure to excess trimethylphosphite in acetonitrile at 60° C.

The other component required to assemble the leukotriene skeleton, aldehyde 25, was constructed from δ-valerolactone as follows. δ-Valerolactol was reacted with excess methyl (triphenylphosphoranylidene) acetate in benzene at 25° C. to afford, after Jones oxidation, the α,β-unsaturated ester carboxylic acid 22 (75% overall). Treatment of this monoester (22) with Dibal (2.2 equiv., $Ch_2Cl_2$, −78° C.) followed by esterification with diazomethane gave the allylic alcohol 23 which was smoothly cyclopropanated ($CH_2I_2$—Zn—CuCl, ether, 35° C., 75%) to afford 24, and oxidized with $CrO_3$.pyr.HCl,NaOAc ($CH_2Cl_2$, 25° C.) leading to the aldehyde 25 (90%).

Generation of the lithium salt of phosphonate 20 (1.1 equiv. LDA, THF, −78° C.) and addition of the aldehyde 25 (−78° C.) followed by stirring at 25° C. for 24th, resulted in a highly efficient and stereocontroled coupling, forming compound 26 (65% yield, 7(E):7(Z)≧10, which was decontaminated from minor undesired isomers by flash column chromatography using silver-nitrate impregnated silica (10% ether in petroleum ether). Finally, selective hydrogenation of the acetylenic linkage (Lindlar/hexane/25° C.) led to the methyl ester 27 (90%, $R_f$=0.33, 10% ether in petroleum ether). Hydrolysis of 27 with LiOH—THF—$H_2O$ at 25° C. gave 5,6-methanoleukotriene $A_4$ in essentially quantitative yield ($R_f$=0.38, 50% ether in petroleum ether).

BIOLOGICAL TESTING 5,6-methanoleukotriene $A_4$ is a potent and selective inhibitor of leukotrotriene biosynthesis, as demonstrated by in vitro experiments. When 5,6-methanoleukotriene $A_4$ is added to a preparation of arachidonic acid containing the necessary enzymes, the formation of SRS-A is severely and drastically reduced. On the other hand, the formation of prostaglandins is not, demonstrating continuing functioning of the cyclooxygenase pathway with inhibition of the lipoxygenase one.

What is claimed as new and intended to be protected by Letters Patent of the United States is:

1. A compound of the formula

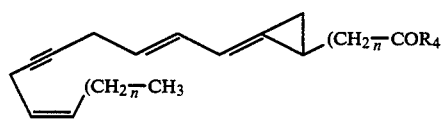

wherein n is 3;
m is 4; and
$R_4$ is methoxy.

* * * * *